(12) United States Patent
Wagner (10) Patent No.: US 10,092,418 B2
(45) Date of Patent: Oct. 9, 2018

(54) TOOLING SYSTEM AND METHOD TO REMOVE A PROSTHETIC HEAD FROM A STEM

(71) Applicant: Zimmer, Inc., Warsaw, IN (US)

(72) Inventor: Terry W. Wagner, Mishawaka, IN (US)

(73) Assignee: Zimmer, Inc., Warsaw, IN (US)

( * ) Notice: Subject to any disclaimer, the term of this patent is extended or adjusted under 35 U.S.C. 154(b) by 424 days.

(21) Appl. No.: 14/826,490

(22) Filed: Aug. 14, 2015

(65) Prior Publication Data

US 2017/0042700 A1 Feb. 16, 2017

(51) Int. Cl.
  *A61B 17/58* (2006.01)
  *A61B 17/60* (2006.01)
  *A61F 2/00* (2006.01)
  *A61F 2/46* (2006.01)
  *A61F 2/36* (2006.01)
  *A61F 2/40* (2006.01)

(52) U.S. Cl.
  CPC .......... *A61F 2/4603* (2013.01); *A61F 2/4607* (2013.01); *A61F 2/4612* (2013.01); *A61F 2/4637* (2013.01); *A61F 2002/365* (2013.01); *A61F 2002/4037* (2013.01); *A61F 2002/4619* (2013.01); *A61F 2002/4641* (2013.01)

(58) Field of Classification Search
  None
  See application file for complete search history.

(56) References Cited

U.S. PATENT DOCUMENTS

| 5,352,227 | A | 10/1994 | O'hara |
| 2007/0005145 | A1* | 1/2007 | Banks ................ A61B 5/6846 623/23.42 |
| 2007/0078464 | A1 | 4/2007 | Jones et al. |

FOREIGN PATENT DOCUMENTS

| DE | 10014401 A1 | 6/2001 |
| JP | H-059520 U | 2/1993 |

OTHER PUBLICATIONS

"International Application Serial No. PCT/US2016/046678, International Search Report dated Nov. 14, 2016", 5 pgs.
"International Application Serial No. PCT/US2016/046678, Written Opinion dated Nov. 14, 2016", 7 pgs.

* cited by examiner

*Primary Examiner* — Sameh Boles
(74) *Attorney, Agent, or Firm* — Schwegman Lundberg & Woessner, P.A.

(57) ABSTRACT

A tooling system and method is disclosed for removing a head portion of a modular implant from a stem portion of the implant. The tooling system can include first and second tools configured to releasably mate together when the upper and lower tools are in an assembled position, and a holder configured to releasably secure the first and second tools in the assembled position. The first and second tools can be inserted between the head portion and an adaptor of the stem portion. When the first and second tools are rotated in opposite directions, the first tool can exert pressure on the head portion of the implant sufficient to release the head portion from locked engagement with the adaptor. The first and second tools can include mating features that disengage from each other as the tools are rotated in opposite directions.

19 Claims, 6 Drawing Sheets

TOOLING SYSTEM AND METHOD TO REMOVE A PROSTHETIC HEAD FROM A STEM

TECHNICAL FIELD

The present application relates to orthopedic prostheses, and more particularly, to tooling systems and methods for removing a prosthetic head of an implant from locked engagement with a prosthetic stem of the implant.

BACKGROUND

Orthopedic procedures are commonly utilized to repair and/or replace damaged bone and tissue in the human body. For example, shoulder replacement may be used to replace all or part of the glenohumeral joint with a prosthetic implant. The glenohumeral joint is a ball and socket joint that includes articulation between the glenoid fossa and the head of the humerus. A shoulder implant can similarly include a humeral component with a hemispherical-shaped head and a stem implantable in the humeral canal, and a glenoid component that includes an articular surface for articulation with the humeral head. The humeral component can be designed such that the humeral head can be in locked engagement with the stem or an adaptor connected to the stem.

There are other types of prosthetic implants that include a ball and socket design that mimics the joint, including, for example, a hip implant. The hip implant can include a stem insertable into the femur and having a ball attached thereto, and a cup attachable to the pelvis.

In some cases, a revision surgery may need to be performed due to, for example, implant failure, infection or damage surrounding the implant. It may be advantageous to leave the original stem implanted in the bone canal of the patient and replace the ball or head. This requires that the ball or head be removed from its locked position on the stem. Impaction, which can have an adverse impact on the patient, is commonly used to break the engagement between the ball or head and the stem.

OVERVIEW

The present inventor recognizes, among other things, an opportunity for minimally invasive tooling and techniques for removing the head of an implant from the stem without impaction or hammering. A removal tooling device can engage with the head and the stem or an adaptor of the stem, to unlock the head from the stem.

To further illustrate the removal tooling device and methods disclosed herein, a non-limiting list of examples is provided here:

In Example 1, a tool configured to aid in removing a head portion of a modular implant from a stem portion comprises a first component comprising a first feature and a second component comprising a second feature configured to correspond with and releasably mate with the first feature of the first component. The mating first and second components can be insertable between the head portion and the stem portion of the modular implant. The first and second components can be moved in opposite directions relative to one another to dislodge the head portion from the stem portion.

In Example 2, the tool of Example 1 is optionally configured such that the first feature comprises a protrusion formed on an inferior side of the first component and the second feature comprises a depression formed on a superior side of the second component.

In Example 3, the tool of Example 2 is optionally configured such that the protrusion is a pair of crescent-shaped protrusions and the depression is a pair of crescent-shaped depressions.

In Example 4, the tool of any one of Examples 1-3 is optionally configured such that the first and second components each further comprise an extension portion configured for engagement by a user of the tool or for attachment to a holder configured to releasably secure the first and second components.

In Example 5, the tool of any one of Examples 1-4 optionally further comprises a holder configured to releasably secure each of the first and second tools to the holder during insertion of the mating first and second components between the head and stem portions of the modular implant.

In Example 6, the tool of any one of Examples 1-5 optionally further comprises first and second handles attachable to the first and second components, respectively, and configured to aid a user in moving the first and second components in opposite directions.

In Example 7, the tool of any one of Examples 1-6 is optionally configured such that the modular implant is implanted in a body of a patient when the first and second components are inserted between the head portion and the stem portion of the modular implant.

In Example 8, the tool of any one of Examples 1-7 is optionally configured such that the tool is configured for use during a revision surgery to replace a portion of the modular implant.

In Example 9, a tooling system configured for removing a head portion of a modular implant from a stem portion of the modular implant can comprise an upper tool having an upper engagement portion and an upper extension portion, and a lower tool having a lower engagement portion and a lower extension portion. The upper and lower engagement portions can each include corresponding mating features to releasably mate together when the upper and lower tools are in an assembled position. The tooling system can further comprise a holder configured to releasably secure the upper and lower extension portions to the holder in the assembled position. The upper and lower tools can be insertable in the assembled position between the head portion of the modular implant and an adaptor of the stem portion. The upper and lower tools can be rotated in opposite directions to move from the assembled position to a separated position and release the head portion from locking engagement with the adaptor.

In Example 10, the tooling system of Example 9 is optionally configured such that the upper tool includes at least one protrusion on an inferior side of the upper tool, and the lower tool includes at least one corresponding depression on a superior side of the lower tool.

In Example 11, the tooling system of Example 10 is optionally configured such that the at least one protrusion includes a pair of helically shaped protrusions.

In Example 12, the tooling system of any one of Examples 9-11 is optionally configured such that the upper tool includes an inclined portion disposed between the upper engagement portion and the upper extension portion.

In Example 13, the tooling system of any one of Examples 9-12 is optionally configured such that the lower and upper engagement portions each include a cut-out sized and shaped to engage with the adaptor of the modular implant.

In Example 14, the tooling system of any one of Examples 9-13 is optionally configured such that at least one of the lower and upper extension portions include a feature configured to engage with a corresponding feature on the holder.

In Example 15, the tooling system of Example 14 is optionally configured such that the feature on the holder creates a friction fit between the holder and at least one of the lower and upper extension portions.

In Example 16, the tooling system of any one of Examples 9-15 optionally further comprises an upper handle configured to removably attach to the upper tool and a lower handle configured to removably attach to the lower tool. The upper and lower tools can be gripped by a user in rotating the upper and lower tools in opposite directions.

In Example 17, the tooling system of any one of Examples 9-16 is optionally configured such that the modular implant includes at least one of a shoulder implant and a hip implant.

In Example 18, a method of removing a head portion of a modular implant from a stem portion of the modular implant comprises providing a first mating tool having a first engagement portion and a first extension portion, and providing a second mating tool having a second engagement portion and a second extension portion. The method can further include assembling the first and second mating tools together by mating a first feature on the first engagement portion with a second feature on the second engagement portion, inserting the first and second mating tools between the head portion and the stem portion of the modular implant, and rotating the first and second mating tools in opposite directions to disassemble the first and second mating tools from each other and remove the head portion from the stem portion of the modular implant.

In Example 19, the method of Example 18 is optionally configured such that the assembled first and second mating tools are releasably secured to a holder prior to inserting the first and second mating tools between the head portion and the stem portion of the modular implant.

In Example 20, the method of Example 18 or 19 optionally further comprises attaching a first handle to the first mating tool and a second handle to the second mating tool, prior to rotating the first and second mating tools in opposite directions.

In Example 21, the method of any one of Examples 18-20 is optionally configured such that the first mating tool includes a crescent-shaped protrusion on an underside of the first engagement portion and the second mating tool includes a crescent-shaped depression on a top surface of the second engagement portion.

In Example 22, the method of any one of Examples 18-21 is optionally configured such that the first and second engagement portions each include a cut-out portion configured to receive the head portion of the modular implant when the first and second mating tools are inserted between the head and stem portions of the modular implant.

In Example 23, the system or method of any one or any combination of Examples 1-22 can optionally be configured such that all elements or options recited are available to use or select from.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present tooling systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to devices and methods for removing the head of a prosthetic implant from the stem of the implant, such as during an arthroplasty and/or revision surgery. The implant can be any type of implant having a ball and socket type design, including, but not limited to, a hip implant or a shoulder implant.

Figure 1:
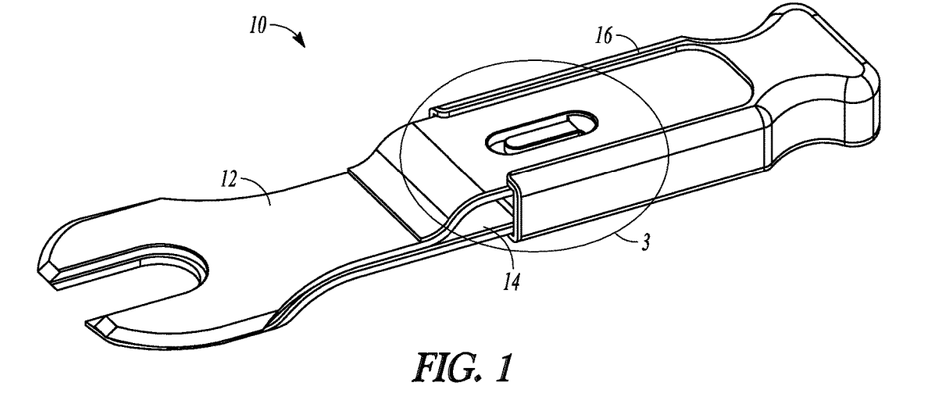
FIG. 1 is a perspective view of a tooling system which includes an upper tool, a lower tool and a holder.

FIG. 1 illustrates an example of a tooling system 10 configured to remove a head of a prosthetic implant from locked engagement (such as a taper lock) with a portion of the stem of the implant. The head can be in locked engagement with an adaptor integral with or connected to the stem of the implant. In an example, the tooling system 10 can be used after the implant has been placed in a patient's body, such as during the arthroplasty procedure, or at a later time, for example, as part of a revision procedure. The tooling system 10 can include two tooling pieces, which can be described herein as an upper tool 12 and a lower tool 14, and a holder 16. The tooling pieces can alternatively be described as a first tool or first component 12 and a second tool or second component 14.

Figure 2:
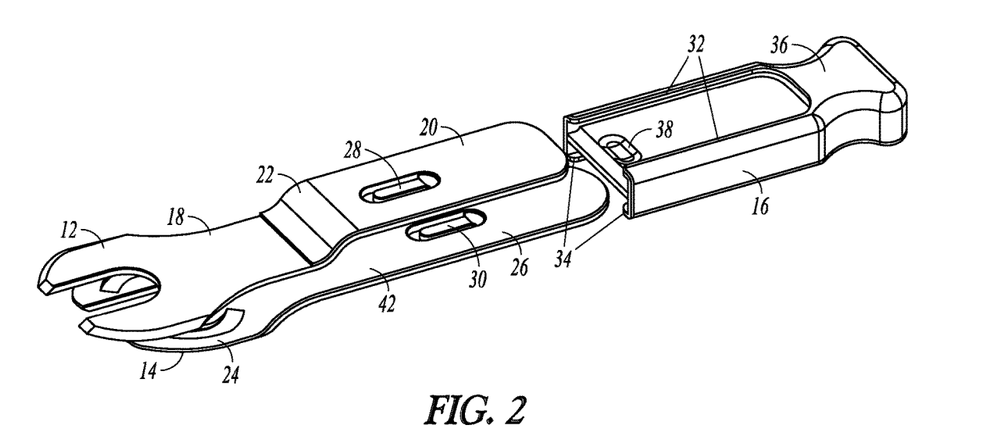
FIG. 2 is an exploded view of the tooling system of FIG. 1.

FIG. 2 is an exploded view of the tooling system 10 of FIG. 1. The upper tool 12 can include an upper engagement portion 18, an upper extension portion 20 and an inclined portion 22 located therebetween. The lower tool 14 can include a lower engagement portion 24 and a lower extension portion 26. As described further below, the upper 18 and lower 24 engagement portions of the upper 12 and lower 14 tools, respectively, can be configured to engage with a prosthetic implant having a head that is to be removed from a remaining portion of the implant. One or both of the upper 12 and lower 14 tools can include a feature 28 and 30, respectively, for engagement with the holder 16, as described further below in reference to FIG. 3.

The upper 18 and lower 24 engagement portions of the upper 12 and lower 14 tools, respectively, can include mating features which facilitate releasable mating of the upper 12 and lower 14 tools with each other. This can be referred to as an assembled position. An inferior side 40 of the upper tool 12 (see FIG. 5) can include a male or female feature configured to mate with a corresponding male or female feature on a superior side 42 of the lower tool 14. When the upper 12 and lower 14 tools are mated together, the engagement portions 18 and 24 are essentially flush with one another (as shown in FIG. 1) and a portion of the tooling device 10 can be temporarily inserted into a body of a patient as described below. The mating features of the upper 12 and lower 14 tools are also described further below.

The holder 16 can be configured to maintain the engagement between the tools 12 and 14 in the assembled position and aid the user in handling the tools 12 and 14. The holder 16 can include a first pair of slots 32 and a second pair of slots 34 located on an opposing side of the holder 16. Each pair of slots 32 and 34 can be configured to receive the extension portions 20 and 26 of the upper 12 and lower 14 tools, respectively. The holder 16 can also include an end portion 36 configured for gripping by a user of the tooling system 10.

The upper tool 12 can include the inclined portion 22 such that the upper 20 and lower 26 extension portions are separate and not in contact when the upper 12 and lower 14 tools are in an assembled position, whereas the upper 18 and lower 24 engagement portions are flush with each other in the assembled position. In another example, the lower tool 14 can include an inclined portion as an alternative to or in addition to the inclined portion 22 of the upper tool 12.

Figure 3:
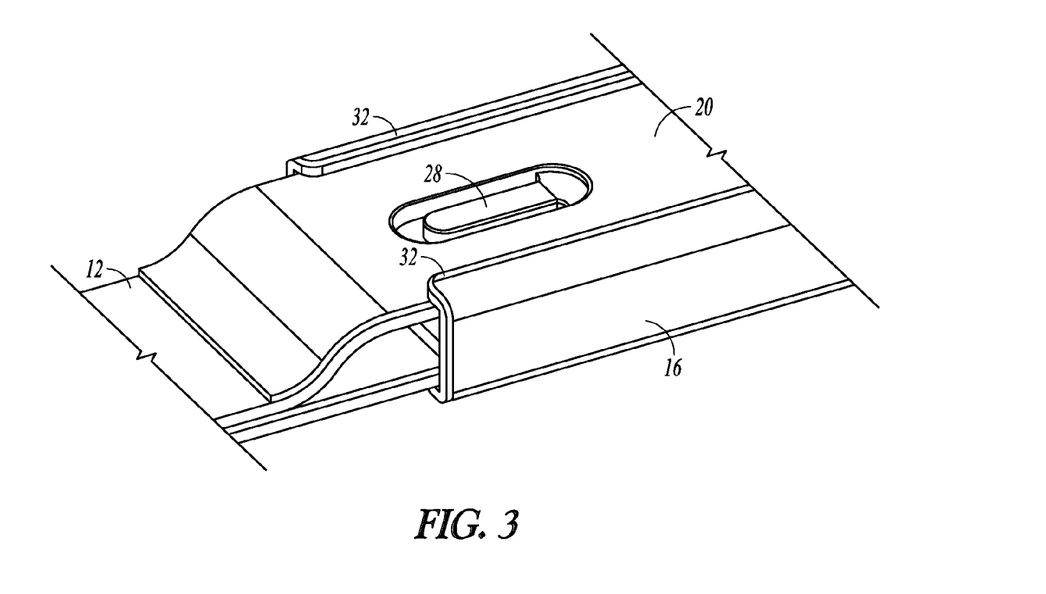
FIG. 3 is a perspective view of a portion of the tooling system of FIG. 1.

As further illustrated in FIG. 3, the upper 12 and lower 14 tools can be releasably secured to the holder 16, for example, by inserting the extension portions 20 and 26 into the slots 32 and 34, respectively, of the holder 16. One or both of the features 28 and 30 on the upper 12 and lower 14 tools can engage with a feature on one or both sides of the holder 16. A friction fit can be created between the tool 12 or 14 and the holder 16 to hold the tools 12 and 14 to the holder 16 until the user wants to release the tools 12 and 14 from the holder 16. Although the figures show both the upper 12 and lower 14 tools including a feature for engagement with the holder 16, it is recognized that only one of the tools 12 or 14 could include such feature. Moreover, it is recognized that the tooling system 10 can include other types of features or designs, in addition to or as an alternative to those described above and shown in the figures, to releasably secure the upper 12 and lower 14 tools to the holder 16.

In an example, the upper 12 and lower 14 tools can mate with each other and then be inserted into the slots 32 and 34 of the holder 16 to releasably secure the upper 12 and lower 14 tools to the holder 16. In another example, the upper 12 and lower 14 tools can be separately inserted into the slots 32 and 34, respectively, and then the upper 12 and lower 14 tools can be mated together.

Figure 4:
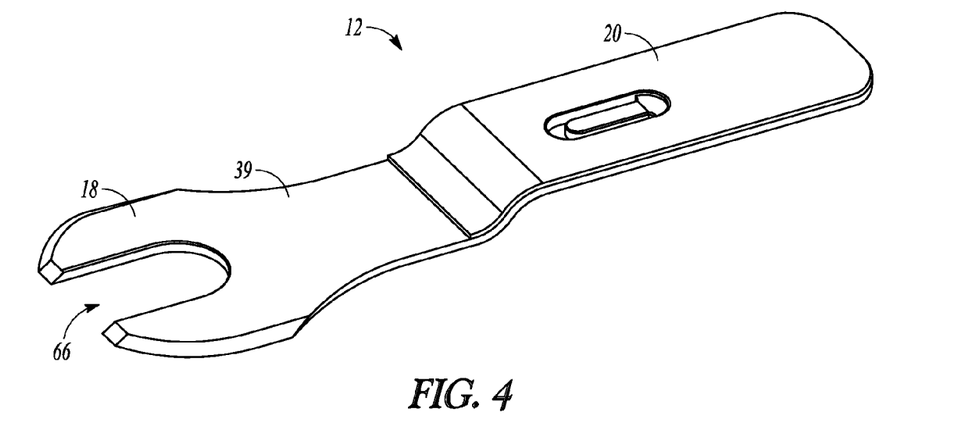
FIG. 4 is a perspective view of a superior side of the upper tool of FIG. 1.
Figure 5:
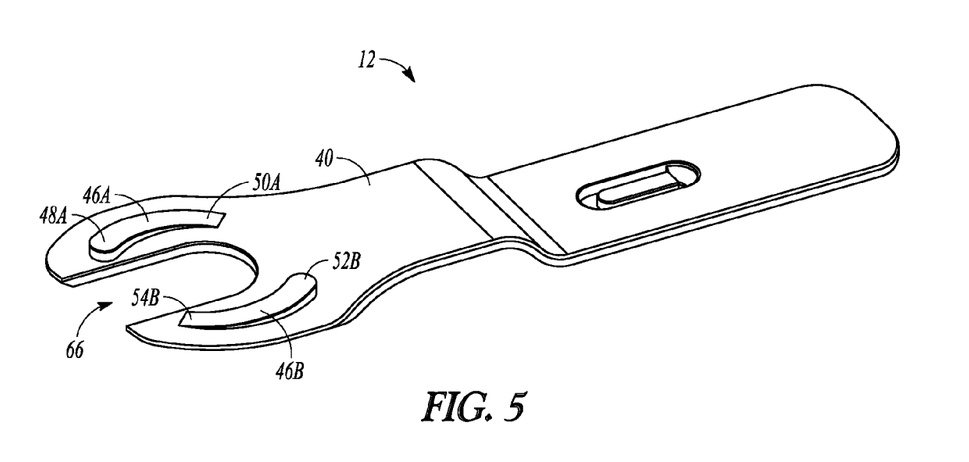
FIG. 5 is a perspective view of an inferior side of the upper tool of FIG. 4.
Figure 6:
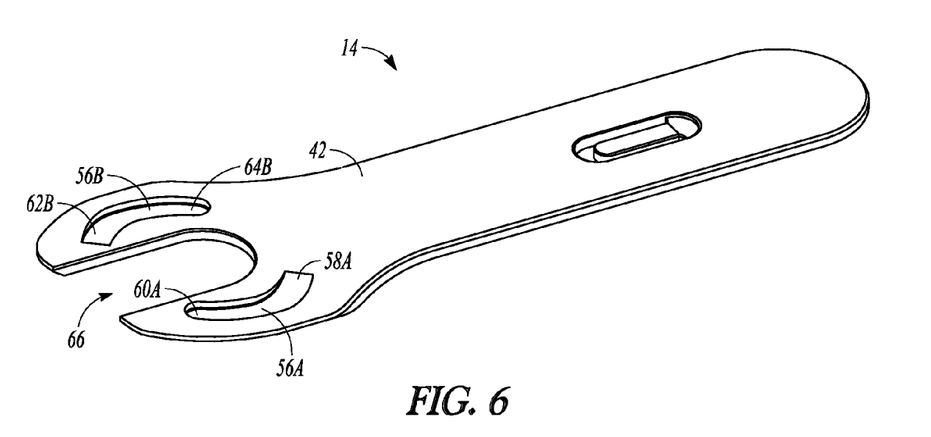
FIG. 6 is a perspective view of a superior side of the lower tool of FIG. 1.
Figure 7:
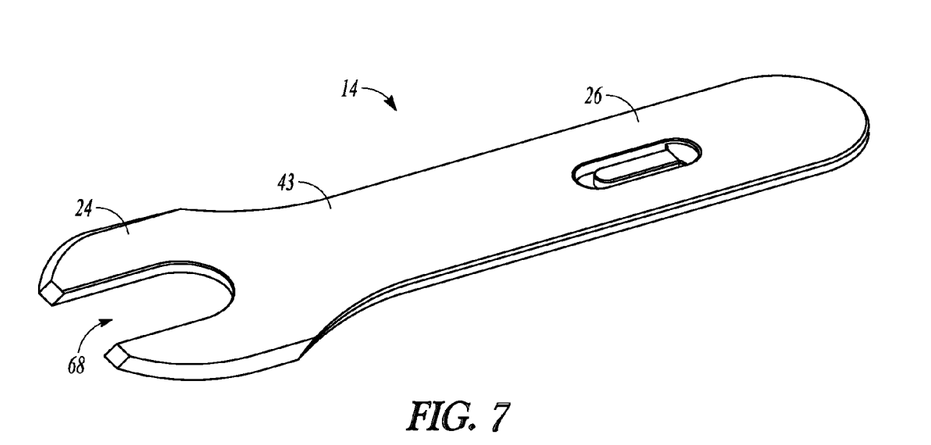
FIG. 7 is a perspective view of an inferior side of the lower tool of FIG. 6.

The upper 12 and lower 14 tools are described in more detail in reference to FIGS. 4-7. FIG. 4 illustrates a superior side 39 of the upper tool 12 and FIG. 5 illustrates the inferior side 40 of the upper tool 12. FIG. 6 illustrates the superior side 42 of the lower tool 14 and FIG. 7 illustrates an inferior side 43 of the lower tool 14.

One or more male features can be formed in the inferior side 40 of the upper tool 12 and one or more corresponding female features can be formed in the superior side 42 of the lower tool 14. In an example, the upper tool 12 can include a pair of protrusions 46A and 46B, and each protrusion 46A and 46B can have a crescent or helical shape. Each protrusion 46A and 46B can have a ramped configuration such that a thickness or height of the protrusion, measured in a proximal/distal direction, can vary across a length of the protrusion 46A or 46B. A first end 48A of the protrusion 46A can have a thickness or height greater than a thickness or height of the protrusion 46A at a second end 50A; similarly, a first end 52B of the protrusion 46B can have a thickness or height greater than a thickness or height of the protrusion 46B at a second end 54B. In an example, the protrusions 46A and 46B can be asymmetrically oriented to each other and the first end 48A of the protrusion 46A can be located at a diagonal position to the first end 52B of the protrusion 46B.

The lower tool 14 can include a pair of depressions 56A and 56B, and each depression 56A and 56B can have a crescent or helical shape corresponding to a respective protrusion 46A and 46B, respectively, of the upper tool 12. The depressions 56A and 56B can be configured to receive or mate with the protrusions 46A and 46B, respectively, of the upper tool 12. Each depression 56A and 56B can have a varying thickness across a length of the depression 56A and 56B. Thus the depressions 56A and 56B can also have a ramped configuration. A first end 58A of the depression 56A can have a thickness, measured in a proximal/distal direction, greater than a thickness of the depression 56A at a second end 60A; similarly, a first end 62B of the depression 56B can have a thickness greater than a thickness of the depression 56B at a second end 64B. To correspond with the protrusions 46A and 46B, the depressions 56A and 56B can similarly be asymmetrically oriented to each other.

The upper engagement portion 18 of the upper tool 12 can include a recess or cut-out 66 configured for engagement with an implant as described further below. The lower engagement portion 24 of the lower tool 14 can similarly include a corresponding recess or cut-out 68. The cut-outs 66 and 68 can be configured to accommodate adaptors and head portions of various sizes. The size or shape of the cut-outs 66 and 68 can vary depending on a size and shape of the adaptor that is engaged with the head portion of the implant. Tools 12 and 14 having various cut-out designs can be available, for example, in a kit or provided separately. In an example, the tools 12 and 14 can have a modular design, such that the engagement portions 18 and 24 can be releasably connected to the extension portions 20 and 26, respectively, so that the engagement portions 18 and 24 can be detachable from the extension portions 20 and 26, respectively, and interchangeable based on the design of the particular implant.

The mating of the protrusions 46A and 46B with the corresponding depressions 56A and 56B can result in the engagement portions 18 and 24 of the first 12 and second 14 tools being flush with each other in the assembled position. The thick portion of the protrusion 46A at the end 48A can align with the thick portion of the depression 56A at the end 60A. Moving the upper 12 and lower 14 tools from the assembled position to a disassembled position is described below. In another example, the upper tool 12 can be configured to include depressions in the inferior side 40 and the lower tool 14 can be configured to include protrusions in the superior side 42.

In an example, the upper 12 and lower 14 tools can be formed of one or more metals or metal alloys. In an example, the upper 12 and lower 14 tools can be formed of different materials, relative to each other, or formed of the same material, but with dissimilar properties. For example, different levels of heat treatment can be applied to the same material to form the upper tool 12 having dissimilar properties relative to the lower tool 14. The material can be selected, at least in part, based on strength and elasticity. In an example, one or both of the upper 12 and lower 14 tools can be formed of 17-4 stainless steel or titanium. The holder 16 can also be formed of one or more metals or metal alloys. In an example, the holder 16 can be formed of a plastic or a metal, or other types of materials that are resistant to rust and able to handle some impaction.

Use of the tooling system 10 is described below, and illustrated in FIGS. 8-10, in the context of a modular shoulder implant. The tooling system can be used to remove the head of the shoulder implant from the stem portion of the implant. It is recognized that the tooling system 10 can be used with other prosthetic implants configured to replace a ball and socket type joint. For example, the tooling system 10 can be used with a hip implant in which a femoral head is attached to an adaptor of the femoral stem.

Figure 8:
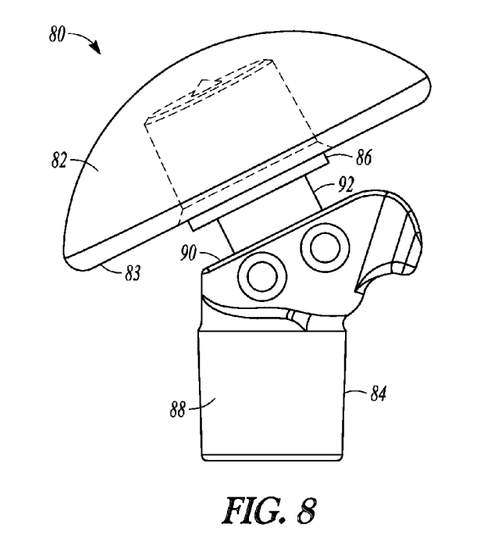
FIG. 8 is a perspective view of a head and an adaptor configured for use with a stem of an implant.

FIG. 8 illustrates components of a shoulder implant 80, including a head portion or humeral head 82 attached to an adaptor 84. In an example, a taper lock can be used to releasably secure the head 82 to the adaptor 84. The adaptor 84 can be configured to lock onto a stem (not shown) of the implant 80. For simplicity, only the humeral head 82 and adaptor 84 are shown in FIGS. 8-10; however, it is recognized that the stem of the implant 80 can be implanted in a humeral canal of the patient and the adaptor 84 and head 82 can be attached thereto. In another design of the shoulder implant, the adaptor and stem can be a one-piece design in which the adaptor is integral with the stem or the stem can include a tapered portion at the end that functions as an adaptor.

The humeral head 82 is shown in phantom in FIG. 8 to better illustrate engagement between the humeral head 82 and the adaptor 84. The adaptor 84 can include a head-engaging portion 86 and a stem-engaging portion 88. A ledge 90 can be formed between the head-engaging portion 86 and the stem-engaging portion 88. In an example, the humeral head 82 can taper lock to the adaptor 84. Similarly, the adaptor 84 can taper lock to the stem (not shown). In some cases, it may be necessary or desirable to remove the humeral head 82 from locking engagement with the adaptor 84. If the adaptor 84 and corresponding stem are implanted in the humeral canal of the patient, it can be difficult to remove the humeral head 82 from the adaptor 84, given, for example, limitations on space and access to the humeral head 82 in the patient. Moreover, it may be important to minimize physical impact on the patient in removing the head 82 from the adaptor 84.

Figure 9:
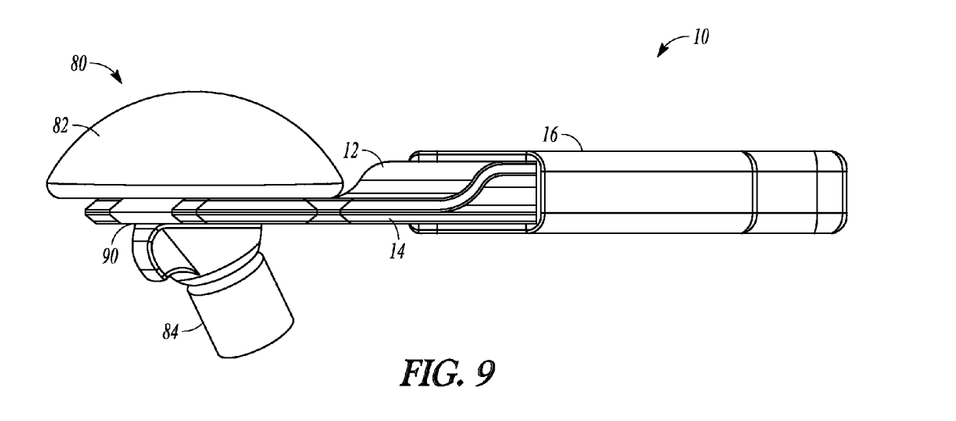
FIG. 9 is a perspective view of the head and adaptor of FIG. 8, with the tooling system of FIG. 1 inserted therebetween.
Figure 10:
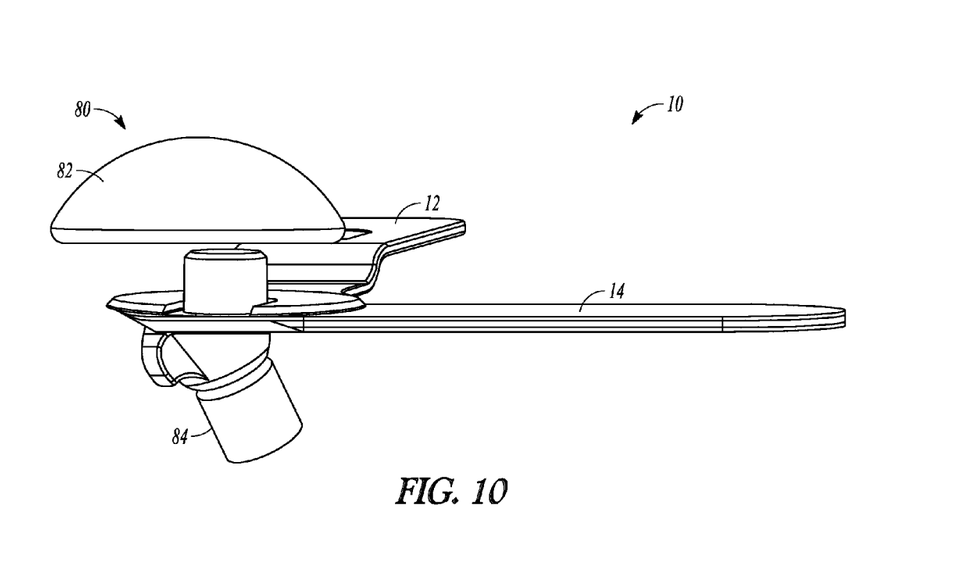
FIG. 10 is a perspective view of the head, adaptor and tooling system of FIG. 9 after the upper tool has been rotated and the head is removed from the adaptor.

FIG. 9 illustrates placement of the first 12 and second 14 tools between the humeral head 82 and adaptor 84. The first 12 and second 14 tools can be in the assembled position during placement and the holder 16 can be used to aid in maintaining the tools 12 and 14 in the assembled position. The first 12 and second 14 tools can be inserted between the head 82 and adapter 84 by engaging the cut-outs 66 and 68 (see FIGS. 4-7) of the tools 12 and 14, respectively, with the head-engaging portion 86 of the adaptor 84. In an example, the cut-outs 66 and 68 can receive a connector portion 92 of the head-engaging portion 86, and the inferior surface 43 of the lower tool 14 can rest on the ledge 90. After insertion of the first 12 and second 14 tools, the holder 16 can be removed from engagement with the first 12 and second 14 tools.

Once the holder 16 is removed, the user of the tooling system 10 can separately grasp each of the tools 12 and 14. Given the configuration of the first tool 12 having the inclined portion 22, each of the extension portions 20 and 26 can be separately handled by the user. The user can then rotate one or both of the tools 12 and 14 in an opposite direction relative to the other tool 12 or 14. In an example, the upper tool 12 can be rotated by the user in a counter-clockwise direction and the lower tool 14 can be generally stationary. In another example, the upper tool 12 can be rotated by the user in the counter-clockwise direction and the lower tool 14 can simultaneously be rotated by the user in a clockwise direction. The orientation of the protrusions 46A and 46B on the upper tool 12 and the depressions 56A and 56B on the lower tool 14 can control a direction that the upper tool 12 can be rotated relative to the lower tool 14. With the design shown in the figures, the upper tool 12 can be rotated counter-clockwise relative to the lower tool 14. If the protrusions 46A and 46B were reversed in orientation on the upper engagement portion 18 (and the depressions 56A and 56B were also reversed accordingly), the upper tool 12 would be rotated clockwise relative to the lower tool 14.

The design of the male and female features on the upper 12 and lower 14 tools can facilitate rotation of the upper 12 and lower 14 tools relative to one another. As described above, the asymmetrically-oriented protrusions 46A and 46B can mate with the depressions 56A and 56B in the assembled position. As the tools 12 and 14 are rotated relative to each other, as described above, the male and female features can become disengaged from each other (the disassembled position). Rotating the tools 12 and 14 from the assembled position to the disassembled position can be similar to unthreading two parts having a threaded engagement with each other. The protrusions 46A and 46B can have a helical design such that the protrusions 46A and 46B can function as short threads. As the tool 12 rotates relative to the tool 14, each of the protrusions 46A and 46B can move up the ramp formed by the respective depression 56A or 56B and the tools 12 and 14 are no longer flush with one another. Because the thickness of the depressions 56A and 56B decreases as the protrusions 46A and 46B move up the ramp of the depressions 56A and 56B, a distance between the tools 12 and 14 progressively increases until the tools 12 and 14 are disassembled from one another.

When the assembled tools 12 and 14 are inserted on the adaptor 84, as shown in FIG. 9, the superior surface 39 of the upper tool 12 can be engaged with a bottom surface 83 of the humeral head 82. As the upper tool 12 rotates and the protrusions 46A and 46B move up the ramps of the depressions 56A and 56B, the height differential between the tools 12 and 14 increases and the upper tool 12 exerts pressure on the bottom surface 83 of the head 82. At some point in the rotation, the pressure from the upper tool 12 is sufficient to overcome the compression that locks the head 82 on the adaptor 84 and the head 82 becomes unlocked from its engagement with the adaptor 84. In other words, the rotation of the tool 12 can cause the head 82 to pop off of the adaptor 84. FIG. 10 shows the upper tool 12 rotated and the humeral head 82 popped off of the adaptor 84.

To be able to insert the tooling system 10 between the humeral head 82 and the adaptor 84, some cortical bone may have to be removed from a medial side of the implant. The amount of bone removed can depend, in part, on a thickness of the tools 12 and 14 in the assembled position, and the position of the implanted humeral head relative to the resection line. In an example, approximately 4 mm of cortical bone can be removed. If the humeral head 82 is located up against the bone, it can be acceptable to remove approximately 4 mm of cortical bone in a revision procedure. After the initial bone removal, the tooling system 10 can be inserted and the proceeding steps for removing the humeral head 82 can be non-invasive.

The thickness of the upper 12 and lower 14 tools can depend, in part, on the height differential (or a distance of travel by the head 82 in a proximal/distal direction) to pop the head 82 off of the adaptor 84 or the stem (if the head is locked directly to the stem). It is recognized that the height differential can depend on a distance between the bottom surface of the head 82 and the opposing surface, when the head is in locked engagement with the adaptor or stem. This distance can vary depending on a particular implant design.

In an example, a total thickness of the upper 12 and lower 14 tools in the assembled position can be between about 3 and 4 mm. In an example, each tool can have a thickness between about 1.5 and 2 mm, which in the case of the upper tool 12 can include the protrusions 46A and 46B. In an example, a thickest portion of the depressions 56A and 56B can range from about 0.5 mm up to about 1.5 mm, and a thickest portion of the protrusions 46A and 46B can range from about 0.5 mm up to about 1.5 mm. The thickness of the protrusions 46A and 46B and depressions 56A and 56B, and consequently the total thickness of each of the tools 12 and 14, can be more or less depending on if more or less travel of the head 82 is needed to pop the head 82 off of the adaptor 84 or stem. It is recognized that the thickness values provided herein are exemplary and the tools 12 and 14 can be designed to have thicknesses less than or greater than the values provided above.

A high tensile strength material can be selected for the tools 12 and 14 such that a thickness of the upper 18 and lower 24 engagement portions, excluding the protrusions 46A and 46B and the depressions 56A and 56B, can be minimized. It can be beneficial to design the tools 12 and 14 such that the tools 12 and 14 are thick enough to exert sufficient pressure on the head 82 and cause the height change or travel described above to remove the head 82 from the adaptor 84, but avoid extra thickness in the design since it can result in unnecessary bone removal in order to insert the tooling system 10.

As stated above, the tooling system 10 can be used in a revision procedure when a part of the implant is to be removed and replaced. In an example, the stem portion of the implant can remain inside the canal during and after the revision procedure and the head portion of the implant can be removed, as described above. The tooling system 10 can allow for easy removal of the head portion from the remaining portion of the implant.

In an example, the tooling system 10 can be used during an arthroplasty procedure after the implant is initially implanted in the body of the patient, and if it is determined, for example, that the head of the implant is not the proper size or design. The tooling system 10 can be used to remove the head and a replacement head can then be locked on the adaptor.

Adapters, similar to the adapter 84, but having varying angles of the head-engaging portion 86 relative to the stem, can be used with the tooling system 10. Regardless of this angle, the first 12 and second 14 tools can be inserted and engage with the adaptor 84. The tooling system 10 can be well-suited for use with an prosthetic implant, such as a shoulder implant or a hip implant, that has a modular design. The modular design can include, for example, various sizes and designs of the adaptor and the humeral head, which can be interchangeable with each other and used with various stems.

The tooling system 10 can be provided in a kit for performing an arthroplasty procedure or a revision procedure, or the tooling system 10 can be separately provided. After the tooling system 10 is used as described above, the tooling system 10 can be sterilized and reused.

In an example, the tooling system 10 can be used as part of a reverse shoulder procedure. In that case, the humeral head can be removed from the adaptor, and the adaptor can be removed using a different type of tooling. A tray can replace the humeral head for attachment to the stem of the implant.

Figure 11:
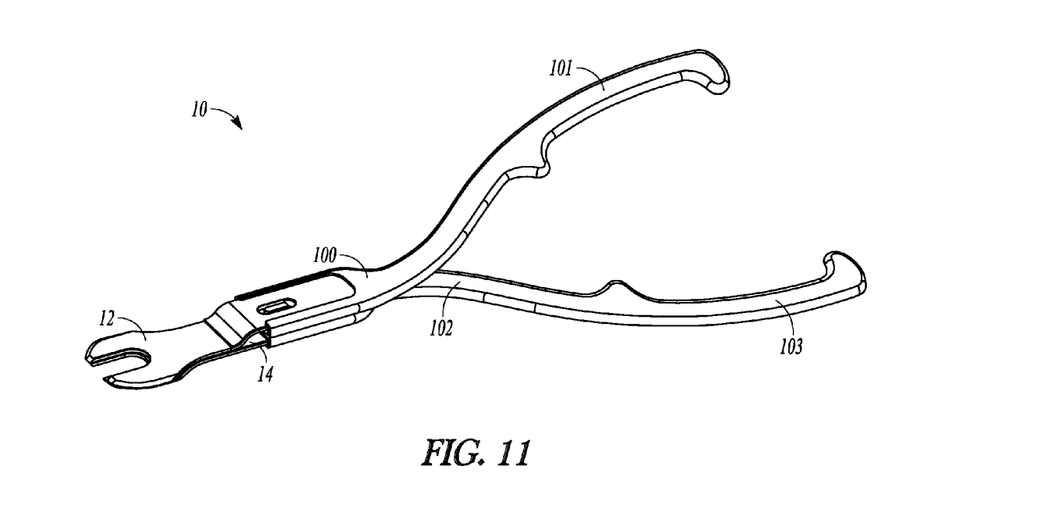
FIG. 11 is a perspective view of first and second handles of the tooling system of FIG. 1 in use with the upper and lower tools.

FIG. 11 illustrates an example of optional components of the tooling system 10. The tooling system 10 can include a first handle 100 and a second handle 102. In an example, each of handles 100 and 102 can be attached to one of the upper 12 and lower 14 tools, after the tools 12 and 14 are in position between the adaptor 84 and the head 82 as shown in FIG. 9, after the holder 16 is removed, and before the tools 12 and 14 are rotated. In an example, the handles 100 and 102 can have a design similar to the holder 16—each of the handles 100 and 102 can include a pair of slots that can receive the respective tool 12 and 14 and a feature that can provide friction with the respective tool 12 and 14 to temporarily hold the tool 12 or 14 in place in the handle 100 or 102. The handles 100 and 102 can be grasped by the user at end portions 101 and 103, respectively, such that the handles 100 and 102 can provide additional leverage during rotation of the tools 12 and 14.

The handles 100 and 102 can be attached to the upper 12 and lower 14 tools, respectively, after the tools 12 and 14 are inserted in the body of the patient. As such, the handles 100 and 102 can be slid into engagement with the tools 12 and 14. FIG. 11 shows an exemplary design of the handles 100 and 102; it is recognized that the handles 100 and 102 can be larger or smaller and can include various designs. As described above, the handles 100 and 102 can be configured to facilitate rotation of the upper 12 and lower 14 tools from an assembled position to a disassembled position in order to remove the head from locked engagement with the stem.

The present disclosure includes a method of removing a head portion of a modular implant from a stem portion of the modular implant using the tooling systems described herein. The method can include providing first and second mating tools, each tool comprising an engagement portion and an extension portion, and assembling the first and second mating tools together such that the tools are in an assembled position. In the assembled position, first and second features formed on the mating tools can be engaged with each other. The method can include inserting the first and second mating tools between a head portion and a stem portion of a modular implant. In an example, the modular implant can be previously implanted in the body of the patient and the tools are inserted into the body during a revision procedure. The method can include using a holder attached to the first and second mating tools to insert the tools between the head and stem portions of the implant and then separating the holder from the tools. Once the mating tools are engaged with an adaptor of the stem and with the head portion, the method can include rotating the first and second mating tools in opposite directions to each other to disassemble the first and second mating tools from each other. Such rotation of the tools can be used to move the humeral head and unlock the head from engagement with the adaptor of the stem. After the head is removed from the adaptor, the tools can easily be removed from the body of the patient. Handles can be attached to the first and second mating tools after the tools are inserted into the body and before the tools are rotated, to aid in rotation of the tools.

As described above, the tooling system and method can used in a revision procedure to remove the head from the stem or to remove the head and the adaptor from the stem when performing a revision that includes a reverse shoulder prosthesis. The tooling system and method can also be used if an initial head is placed improperly on the adaptor of the stem or the head is not properly sized and needs to be replaced with a larger or smaller head.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A tool configured to aid in removing a head portion of a modular implant from a stem portion, the tool comprising:
   a first component comprising a first feature; and
   a second component comprising a second feature configured to correspond with and releasably mate with the first feature of the first component, wherein the mating first and second components are insertable between the head portion and the stem portion of the modular implant, and wherein the first and second components are movable in opposite directions relative to one another to dislodge the head portion from the stem portion, wherein the first feature comprises a protrusion formed on an inferior side of the first component and the second feature comprises a depression formed on a superior side of the second component.

2. The tool of claim 1, wherein the protrusion is a pair of crescent-shaped protrusions and the depression is a pair of crescent-shaped depressions.

3. The tool of claim 1, wherein the first and second components each further comprise an extension portion configured for engagement by a user of the tool or for attachment to a holder configured to releasably secure the first and second components.

4. The tool of claim 1, further comprising a holder configured to releasably secure each of the first and second tools to the holder during insertion of the mating first and second components between the head and stem portions of the modular implant.

5. The tool of claim 1, further comprising first and second handles attachable to the first and second components, respectively, and configured to aid a user in moving the first and second components in opposite directions.

6. The tool of claim 1, wherein the modular implant is implanted in a body of a patient when the first and second components are inserted between the head portion and the stem portion of the modular implant.

7. The tool of claim 6, wherein the tool is configured for use during a revision surgery to replace a portion of the modular implant.

8. A tooling system configured for removing a head portion of a modular implant from a stem portion of the modular implant, the tooling system comprising:
   an upper tool having an upper engagement portion, an upper extension portion, and an inclined portion disposed between the upper engagement portion and the upper extension portion;
   a lower tool having a lower engagement portion and a lower extension portion, the upper and lower engagement portions each including corresponding mating features to releasably mate together when the upper and lower tools are in an assembled position; and
   a holder configured to releasably secure the upper and lower extension portions to the holder in the assembled position, the upper and lower tools insertable in the assembled position between the head portion of the modular implant and an adaptor of the stem portion, wherein the upper and lower tools are rotatable in opposite directions to move from the assembled position to a separated position and release the head portion from locking engagement with the adaptor.

9. The tooling system of claim 8, wherein the upper tool includes at least one protrusion on an inferior side of the upper tool, and the lower tool includes at least one corresponding depression on a superior side of the lower tool.

10. The tooling system of claim 9, wherein the at least one protrusion includes a pair of helically shaped protrusions.

11. The tooling system of claim 8, wherein the lower and upper engagement portions each include a cut-out sized and shaped to engage with the adaptor of the modular implant.

12. The tooling system of claim 8, wherein at least one of the lower and upper extension portions include a feature configured to engage with a corresponding feature on the holder.

13. The tooling system of claim 12, wherein the feature on the holder creates a friction fit between the holder and at least one of the lower and upper extension portions.

14. The tooling system of claim 8, further comprising:
   an upper handle configured to removably attach to the upper tool; and
   a lower handle configured to removably attach to the lower tool, wherein the upper and lower handles are grippable by a user in rotating the upper and lower tools in opposite directions.

15. The tooling system of claim 8, wherein the modular implant includes at least one of a shoulder implant and a hip implant.

16. A tool configured to aid in detaching a head portion of an implant from a stem portion of the implant, the tool comprising:
   a first component comprising a first feature; and
   a second component comprising a second feature configured to correspond with and releasably mate with the first feature of the first component, wherein the first feature comprises at least one protrusion or at least one depression, and the second feature comprises the other of the at least one protrusion or the at least one depression for releasably mating with the first feature,
   wherein the first and second components are insertable between the head portion and the stem portion of the modular implant when the first and second components are engaged with each other, and
   wherein the first and second components are rotatable in opposite directions to disengage the first and second features from each other and detach the head portion of the implant from the stem portion of the implant.

17. The tool of claim 16 wherein the first feature comprises a pair of protrusions and the second feature comprises a pair of corresponding depressions.

18. The tool of claim 16 wherein the first feature comprises a pair of depressions and the second feature comprises a pair of corresponding protrusions.

19. The tool of claim 16 further comprising a holder to releasably secure each of the first and second tools to the holder during insertion of the mating first and second components between the head and stem portions of the modular implant.

\* \* \* \* \*